United States Patent
Yang et al.

(10) Patent No.: US 12,402,945 B2
(45) Date of Patent: Sep. 2, 2025

(54) SYSTEMS AND METHODS FOR LASER PULSE MONITORING AND CALIBRATION

(71) Applicant: Boston Scientific Scimed, Inc., Maple Grove, MN (US)

(72) Inventors: Baocheng Yang, Fremont, CA (US); Xirong Yang, Fremont, CA (US); Peter Bull, San Jose, CA (US); Brian Cheng, San Jose, CA (US); Rongwei Jason Xuan, Fremont, CA (US); Jian James Zhang, Lancaster, MA (US); Thomas Charles Hasenberg, Campbell, CA (US); David Pih, Milpitas, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 494 days.

(21) Appl. No.: 17/664,293

(22) Filed: May 20, 2022

(65) Prior Publication Data
US 2022/0378505 A1 Dec. 1, 2022

Related U.S. Application Data

(60) Provisional application No. 63/191,519, filed on May 21, 2021.

(51) Int. Cl.
| | |
|---|---|
| *A61B 18/22* | (2006.01) |
| *A61B 17/00* | (2006.01) |
| *A61B 18/20* | (2006.01) |

(52) U.S. Cl.
CPC ...... *A61B 18/22* (2013.01); *A61B 2017/0019* (2013.01); *A61B 2017/00725* (2013.01);
(Continued)

(58) Field of Classification Search
CPC ............ A61B 18/22; A61B 2017/0019; A61B 2017/00725; A61B 2018/20359;
(Continued)

(56) References Cited

U.S. PATENT DOCUMENTS

| | | | | |
|---|---|---|---|---|
| 4,008,444 A | * | 2/1977 | Zar | ......................... H01S 3/134 |
| | | | | 372/74 |
| 4,982,195 A | * | 1/1991 | Olivenbaum | ......... G01S 13/767 |
| | | | | 342/51 |

(Continued)

FOREIGN PATENT DOCUMENTS

WO 2020159017 A1 8/2020

OTHER PUBLICATIONS

Beers, The Theory of the Optical Wedge Beam Splitter, 1974, National Bureau of Standards, Issue 146, accessed via https://books.google.com/books/about/The_Theory_of_the_Optical_Wedge_Beam_Spl.html?id=QoTUJkWOyNEC (Year: 1974).*

(Continued)

*Primary Examiner* — Jonathan T Kuo
(74) *Attorney, Agent, or Firm* — Seager, Tufte & Wickhem, LLP

(57) ABSTRACT

A medical laser system for outputting laser pulses includes at least one laser cavity configured to generate at least one laser pulse, a rotating mirror configured to receive and reflect the at least one laser pulse, a beam splitter configured to receive and reflect a portion of the at least one laser pulse received from the rotating mirror, an energy-sensing device configured to detect the portion of the at least one laser pulse, an energy measurement assembly configured to generate a feedback signal based on the portion of the at least one laser pulse detected by the energy-sensing device, and a controller configured to generate an electronic control pulse based on the feedback signal received from the energy
(Continued)

measurement assembly to generate at least one adjusted laser pulse.

20 Claims, 7 Drawing Sheets

(52) U.S. Cl.
CPC ............... *A61B 2018/20359* (2017.05); *A61B 2018/20553* (2017.05)

(58) Field of Classification Search
CPC ........... A61B 2018/20553; A61B 2018/00642; A61B 18/20–18/28; H01S 3/1305
See application file for complete search history.

(56) References Cited

U.S. PATENT DOCUMENTS

| | | | | |
|---|---|---|---|---|
| 5,151,909 | A * | 9/1992 | Davenport | H01S 3/117 359/328 |
| 5,367,399 | A * | 11/1994 | Kramer | G02B 26/106 250/236 |
| 5,387,211 | A | 2/1995 | Saadatmanesh et al. | |
| 6,080,148 | A * | 6/2000 | Damasco | A61B 18/22 606/2 |
| 7,999,915 | B2 * | 8/2011 | Ershov | G03F 7/70625 355/53 |
| 11,858,065 | B2 * | 1/2024 | Yao | B23K 26/356 |
| 2008/0165337 | A1 * | 7/2008 | Ershov | G03F 7/70625 430/322 |
| 2019/0072756 | A1 | 3/2019 | Waisman et al. | |
| 2020/0222118 | A1 * | 7/2020 | Yu | A61B 18/20 |
| 2020/0346301 | A1 * | 11/2020 | Yao | B23K 26/20 |

OTHER PUBLICATIONS

Wikipedia, Matrix (mathematics), https://en.wikipedia.org/wiki/Matrix_(mathematics) (Year: 2025).*

International Search Report and Written Opinion for International Application No. PCT/US2022/072470 mailed Sep. 15, 2022.

* cited by examiner

SYSTEMS AND METHODS FOR LASER PULSE MONITORING AND CALIBRATION

CROSS-REFERENCE TO RELATED APPLICATIONS

This application claims the benefit of priority from U.S. Provisional Application No. 63/191,519, filed on May 21, 2021, which is incorporated by reference herein in its entirety.

TECHNICAL FIELD

The present disclosure relates generally to medical/surgical laser systems, and more particularly, to systems and methods for monitoring and calibrating laser pulses with such systems.

BACKGROUND

Medical laser systems are used for a variety of surgical procedures. These procedures may include dusting and/or fragmentation of stones in the kidney, the bladder, and/or the ureter. Medical laser systems are also used to create incisions and to ablate and/or coagulate soft tissues, such as, but not limited to, the prostate. Medical laser systems may output laser pulses having variable characteristics, such as, average power of the output laser pulses, based on preset conditions. For example, a laser pulse having a specific average power level may be generated based on one or more input parameters, such as pulse energy and/or pulse repetition frequency. However, laser pulses generated at each preset average power level needs to be calibrated in order to ensure the accuracy of the output laser pulses.

A medical laser system may be calibrated by measuring the energy of each output laser pulse with an energy sensor, and adjusting the preset conditions of the medical laser system. However, the measured energy of the output laser pulse may be inconsistent based on various factors, such as the incident angle of the laser pulse measured by the energy sensor or operational or manufacturing inconsistencies of the components of the medical laser system that generate the laser pulse.

SUMMARY OF THE DISCLOSURE

Examples of the disclosure relate to, among other things, systems and methods for monitoring and calibrating laser pulses, among other aspects. Each of the examples disclosed herein may include one or more of the features described in connection with any of the other disclosed aspects.

In one example, a medical laser system may be provided for outputting laser pulses. The medical laser system may include: at least one laser cavity configured to generate at least one laser pulse; a rotating mirror configured to receive and reflect the at least one laser pulse; a beam splitter configured to receive and reflect a portion of the at least one laser pulse received from the rotating mirror; an energy-sensing device configured to detect the portion of the at least one laser pulse; an energy measurement assembly configured to generate a feedback signal based on the portion of the at least one laser pulse detected by the energy-sensing device; and a controller configured to generate an electronic control pulse based on the feedback signal received from the energy measurement assembly to generate at least one adjusted laser pulse.

In other aspects, a medical laser system described herein may include one or more of the following features. The medical laser system may include: a memory comprising at least one spectrum matrix; a calibration module coupled to the memory, the calibration module being configured to calibrate the medical laser system based on the feedback signal and the at least one spectrum matrix; and a monitoring and adjustment module coupled to the calibration module and the memory, the monitoring and adjustment module being configured to perform a closed-loop control based on the feedback signal. The controller may be configured to generate the electric control pulse based on a comparison between the feedback signal and a target laser energy level. The controller may be configured to generate the electric control pulse based on a pulse width error value calculated based on the feedback signal and the target laser energy level. The adjusted laser pulse may be generated by adjusting a pulse width level of a laser pulse based on the feedback signal. The at least one adjusted laser pulse may be generated based at least on one or more correction parameters associated with the at least one laser cavity. The energy sensing device may include laser collection optics. The laser collection optics may include at least one of an attenuator, a focusing lens, or an integrating sphere. The energy sensing device may include an optical sensor module configured to be attached to laser collection optics. The optical sensor module may include a pyroelectric sensor and a sensor circuit board. The energy sensing device may be configured to generate an electrical signal based on the detected the portion of the at least one laser pulse. The energy measurement assembly may include a signal transformation module configured to receive an electrical signal from the energy-sensing device. The signal transformation module may include: an inverting operational amplifier circuit; a signal amplification module coupled to the signal transformation module, the signal amplification module including a non-inverting amplifier circuit; and a signal holding and sampling module coupled to the signal amplification module. The signal transformation module may be configured to switch a mode of the inverting operation amplifier circuit between an amplification mode and an integration mode. The signal amplification module may be configured to adjust a gain of the non-inverting amplifier circuit by adjusting a resistance of one or more resistors in the non-inverting amplifier circuit. The at least one laser cavity may include four laser cavities. Each of the at least one laser cavity may include a glass plate arranged at a Brewster Angle. The beam splitter may include a polarization-insensitive coating.

In another example; a method of controlling laser pulses of a medical laser system may be provided. The method may include: detecting, by the medical laser system, a portion of at least one laser pulse generated by at least one laser cavity; generating, by the medical laser system, an electrical signal based on the detected portion of the at least one laser pulse; generating, by the medical laser system, a feedback signal based on the electrical signal; generating, by the medical laser system, an electric control pulse based on the feedback signal; and generating, by the medical laser system, at least one adjusted laser pulse based on the electric control pulse.

In other aspects, a method described herein may include one or more of the following features. The medical laser system may calibrate one or more laser modes based on the feedback signal and at least one spectrum matrix. The medical system may perform a closed-loop control based on the electrical signal based on the detected portion of the at least one laser pulse and the feedback signal. The medical laser system may generate the electric control pulse based on a comparison between the feedback signal and a target laser energy level. The medical laser system may generate the electric control pulse based on a pulse width error value based on the comparison between the feedback signal and the target laser energy level. The medical laser system may generate the electric control pulse by determining an adjusted electric control pulse width based on the pulse width error value. The medical laser system may generate the at least one adjusted laser pulse based at least on one or more correction parameters associated with the at least one laser cavity. The medical laser system may generate the at least one adjusted laser pulse via multiple laser cavities. The medical laser system may generate the feedback signal by switching a mode of an inverting operation amplifier circuit of a signal transformation module between an amplification mode and an integration mode. The medical laser system may generate the feedback signal by adjusting a gain of a non-inverting amplifier circuit of a signal amplification module by adjusting a resistance of one or more resistors in the non-inverting amplifier circuit.

In yet another example, a non-transitory computer-readable medium may store instructions for controlling laser pulses of a medical laser system. The instructions, when executed by one or more processors, may cause the one or more processors to perform operations. The operations may include: transmitting a control signal to detect a portion of at least one laser pulse generated by at least one laser cavity; receiving an electrical signal based on the detected portion of the at least one laser pulse; generating a feedback signal based on the electrical signal; generating an electric control pulse based on the feedback signal; generating at least one adjusted laser pulse based on the electric control pulse; calibrating one or more laser modes based on the feedback signal and at least one spectrum matrix; and performing a closed-loop control based on the electrical signal based on the detected portion of the at least one laser pulse and the feedback signal.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1:
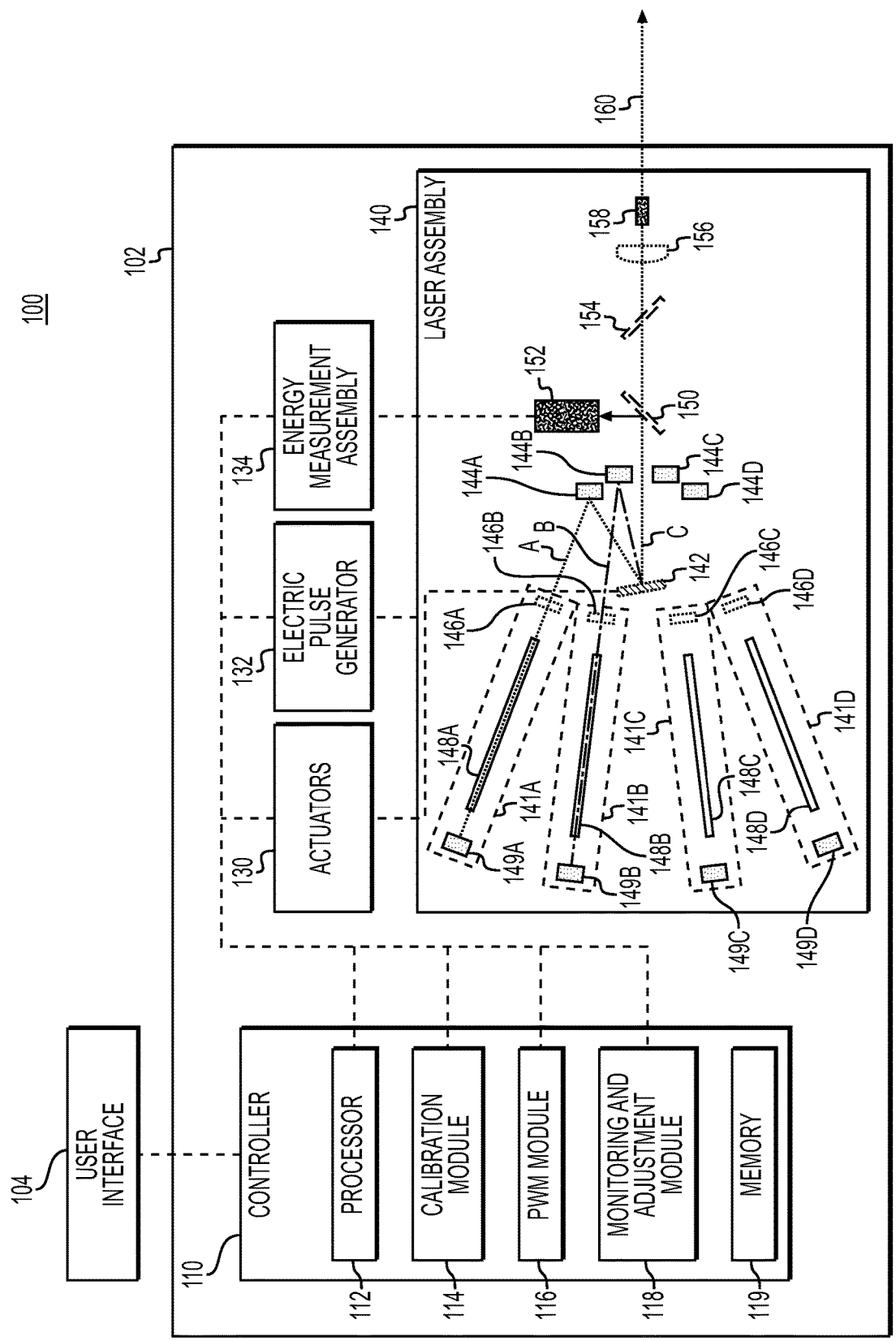
FIG. 1 is a schematic of a medical laser system according to an exemplary embodiment.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

For ease of description, portions of the disclosed devices and/or their components are referred to as proximal and distal portions. It should be noted that the term "proximal" is intended to refer to portions closer to a laser cavity of the laser system, and the term "distal" is used herein to refer to portions further away from the laser cavity of the laser system, e.g., toward an end of a laser fiber that outputs a laser energy. Similarly, extends "distally" indicates that a component extends in a distal direction, and extends "proximally" indicates that a component extends in a proximal direction. Additionally, terms that indicate the geometric shape of a component/surface refer to exact and approximate shapes.

Examples of the disclosure may be used to calibrate, monitor, and/or adjust laser pulses having one or more pulse modes (or shapes) generated by one or more laser cavities of a medical laser system. In some embodiments, the medical laser system may include at least one laser cavity configured to generate at least one laser pulse, and a rotating mirror configured to receive and reflect the at least one laser pulse. Further, the medical laser system may include a beam splitter configured receive and reflect a portion of the at least one laser pulse received from the rotating mirror. In embodiments, the medical laser system may include an energy-sensing device configured to detect the portion of the at least one laser pulse. Further, the medical laser system may include an energy measurement assembly configured to generate a feedback signal based on the portion of the at least one laser pulse detected by the energy pulse sensor. The medical laser system may include a controller configured to generate an electronic control pulse based on the feedback signal received from the energy measurement assembly. In one embodiment, the feedback signal may be utilized to calibrate the medical laser system. In another embodiment, the feedback signal may be utilized to generate control signals used in a closed-loop control process for generating a dynamically adjusted laser.

In some embodiments, the medical laser system of this disclosure may perform monitoring and adjusting of laser pulses based on a closed-loop control process. In one embodiment, the medical laser system may perform the closed-loop control process by detecting a portion of at least one laser pulse generated by at least one laser cavity with an energy-sensing device. The energy sensing device may generate an electrical signal based on the detected portion of at least one laser pulse. In one embodiment, an energy measurement assembly of the medical laser system may generate a feedback signal based on the electrical signal. The feedback signal may be generated by calculating an electric pulse width error value based on the electric signal, and by applying a damping coefficient to the electric pulse width error value. Further, a controller of the medical laser system may generate an adjusted electric control pulse based on the feedback signal. The medical laser system may then generate at least one adjusted laser pulse based on the electric control pulse.

Examples of the disclosure may relate to systems, devices, and methods for performing various medical procedures and/or treating target features, such as tissues of a subject (e.g., a patient). Reference will now be made in detail to examples of the disclosure described above and illustrated in the accompanying drawings. Wherever possible, the same reference numbers will be used throughout the drawings to refer to the same or like parts.

FIG. 1 shows a schematic depiction of an exemplary medical laser system 100 in accordance with an example of this disclosure. The medical laser system 100 may include a laser chassis 102 and a user interface 104. The laser chassis 102 may include a controller 110, actuators 130, an electric pulse generator 132, an energy measurement assembly 134, and a laser assembly 140. The user interface 104 may be communicatively coupled to the controller 110 by, for example, a wired connection, wireless connection, and the like. It should be appreciated that, in some embodiments, the user interface 104 may be a device integral with the medical laser system 100, and in other embodiments, the user interface 104 may be a remote device in communication (e.g., wireless, wired, etc.) with the medical laser system 100. The user interface 104 may include input and output ports to connect with input and output devices such as keyboards, mice, touchscreens, monitors, displays, etc., to receive user inputs and output messages thereon.

Still referring to FIG. 1, the controller 110 may be communicatively coupled to the laser assembly 140 directly, or indirectly via the actuators 130, electric pulse generator 132, and/or the energy measurement assembly 134, by for example, a wired connection, a wireless connection, and the like. For examples, the controller 110 may be a computer system incorporating a plurality of hardware components that allow the controller 110 to receive data (e.g., laser input parameter data, laser sensor data, etc.), process information (e.g., calibration logic or algorithm, PWM scheme logic or algorithm, monitoring, and adjustment logic or algorithm, etc.), and/or generate control signals to generate and output laser pulses via the laser assembly 140. Illustrative hardware components of the controller 110 may include at least one processor 112, at least one calibration module 114, at least one pulse width modulation (PWM) module 116, at least one monitoring and adjustment module 118, and at least one memory 119.

The processor 112, the calibration module 114, the PWM module 116, and the monitoring and adjustment module 118 of the controller 110 may each include any computing device capable of executing machine-readable instructions, which may be stored on a non-transitory computer-readable medium, for example, the memory 119. By way of example, the processor 112, the calibration module 114, the PWM module 116, and the monitoring and adjustment module 118 may each include an integrated circuit, a microchip, a computer, a memory, and/or any other computer processing unit operable to perform calculations and logic operations required to execute a program. As described in greater detail herein, the processor 112, the calibration module 114, the PWM module 116, and the monitoring and adjustment module 118 may each be configured to perform one or more operations in accordance with the instructions stored on the memory 119. The processor 112, the calibration module 114, the PWM module 116, and the monitoring and adjustment module 118 may be communicatively coupled to the actuators 130, the electric pulse generator 132, and the energy measurement assembly 134 in order to facilitate generation and output of laser pulses by the laser assembly 140.

Still referring to FIG. 1, the calibration module 114 may include executable instructions or algorithms that allow the medical laser system 100 to, for example, calibrate the laser pulses generated by the laser assembly 140. The PWM module 116 may include executable instructions or algorithms that allow the PWM module 116 to, for example, generate and transmit PWM control signals to the electric pulse generator 132. The monitoring and adjustment module 118 may include executable instructions or algorithms that allow the monitoring and adjustment module 118 to, for example, monitor and adjust laser pulses based on one or more signals received from the energy measurement assembly 134 and an energy-sensing device 152. In one embodiment, the measurement assembly 134 and the energy-sensing device 152 may be integrated and provided on a single substrate or board. The combination of the measurement assembly 134 and the energy-sensing device 152 may be referred to as an energy measurement board (EMB), hereinafter. The electric pulse generator 132 may generate electric pulses based on one or more signals received from the controller (e.g., signals generated by processor 112, calibration module 114, PWM module 116, monitoring and adjustment module 118, etc.) and transmit the generated electric pulses to one or more laser cavities for generating laser (or optical) pulses.

Still referring to FIG. 1, the laser assembly 140 may include one or more laser cavities 141A-D, each laser cavity being configured to output a laser pulse (or laser beam). Each of the one or more laser cavities 141A-D includes a high reflecting window 149A-D at a proximal end, an output coupler window 146A-D at a distal end, and a chromium thulium holmium-doped YAG (CTH:YAG) laser rod 148A-D disposed between a respective high reflecting window 149A-D and an output coupler window 146A-D. A single laser cavity (e.g., laser cavity 141A, 141B, 141C, or 141D) may produce each laser pulse having a pulse wavelength of, for example, approximately 2 μm, and pulse width in the range of 100 microseconds to a few milliseconds. With a single laser cavity, the laser assembly 140 may operate on a repetition frequency (or rate) at approximately 5 Hertz (Hz) to 20 Hz, and the maximum average power output may be approximately 30 Watts. Since the maximum laser pulse energy capable of being generated by a laser cavity decreases with an increase in the operating repetition frequency of the laser cavity, multiple laser cavities may be utilized to achieve greater average power output at relatively higher repetition frequencies (e.g., approximately 20 Hz to 80 Hz). For example, to ablate tissue and to create a high enough heat to destroy objects, such as kidney stones, it may be necessary to increase the repetition frequency of an output laser pulse by utilizing multiple laser cavities. That is, the controller 110 may excite each of the multiple laser cavities 141A-D at different times and may rotate rotating mirror 142 in a synchronized manner to match each laser pulse generated by the one or more laser cavities 141A-D. As such, each laser pulse generated by each laser cavity may be combined to produce an output laser pulse having an overall repetition rate of up to approximately 80 Hertz, yielding maximum average power that may be greater than 100 Watts.

Still referring to FIG. 1, each CTH:YAG laser rod 148A-D may generate a laser pulse for each of the laser cavities 141A-D, which is directed to a corresponding relay mirror 144A-D along a laser path (e.g., a laser path A, B, etc.). Each laser pulse is reflected from a respective one of the relay mirrors 144A-D to the rotating mirror 142 (e.g., a Galvo mirror) along respective laser paths. The rotating mirror 142 may be configured to rotate about an axis, based on one or more control signals received, for example, from the actuators 130, to face each of the relay mirrors 144A-D and to receive the laser pulses generated by each laser cavity 141A-D. The rotating mirror 142 may reflect each laser pulse from the laser cavities 141A and 141B along the same laser path C to a beam splitter 150 and a beam combiner 154. In one embodiment, the beam splitter 150 may split the laser pulse received via the rotating mirror 142 and transmit a portion of the laser pulse to the energy-sensing device 152. The energy measurement assembly 134 may receive the pulse signals detected by the energy-sensing device 152 and may transmit the received pulse signals to the controller 110 for further processing. The beam combiner 154 may combine the laser pulses received from one or more laser cavities 141A-D via the rotating mirror 142. The beam combiner 154 may have a high transmission characteristic for an output laser beam (e.g., a laser pulse having a wavelength of approximately 2.1 um), and a high reflection characteristic for an aiming beam (e.g., an aiming beam having a wavelength of approximate 0.53 um). Further, the beam combiner 154 may combine the output laser beam with the aiming beam that may be incident perpendicular to that of the output laser beam. Furthermore, the beam combiner 154 may compensate for the transverse shift of the output laser beam introduced by the beam splitter 150. The combined laser pulses may be passed along the laser path C to a coupling lens 156. The coupling lens 156 may couple the combined laser pulses to an output fiber 158, to be transmitted as an output laser pulse (or pulses) 160 to a delivery location. The coupling lens 156 may be any material suitable for coupling the laser light to output fiber 158, including but not limited to a sapphire. The coupling lens 156 may have a focal length of approximately 19 millimeters but is not limited thereto.

In one exemplary embodiment, a laser pulse from the laser cavity 141A may be reflected from the relay mirror 144A to the rotating mirror 142 along the laser path A. Similarly, a laser pulse from the laser cavity 141B may be reflected from the relay mirror 144B to the rotating mirror 142 along the laser path B. The rotating mirror 142 may synchronously reflect each laser pulse from the laser cavities 141A and 141B along the same laser path C to the beam splitter 150 and the beam combiner 154. In this example, the overall repetition frequency of the laser cavities 141A and 141B may be between approximately 10 Hz and 40 Hz. Of course, different combinations of laser cavities may be utilized to achieve a desired laser pulse output at different repetition frequencies (or rates).

Still referring to FIG. 1, the medical laser system 100 of this disclosure may generate output laser pulses having different average power levels. The average power of a laser pulse may be characterized by a repetition frequency and pulse energy associated with one or more laser cavities 141A-D. For various medical applications, users (or operators) may preset laser pulse energy, repetition frequency, the number of laser cavities desired to be used, etc. In one embodiment, all available average power output levels for laser pulses may be programmed and stored, for example, in the memory 119. A complete spectrum of the available average power output of the system 100 may be provided in one or more discrete spectrum matrices, which may be characterized by pulse energy, overall pulse repetition rates, and average optical power. The following table shows an exemplary spectrum matrix (i.e., Pulse Energy Repetition Frequency (PRF) matrix), highlighting one example of available average power levels for given repetition frequencies and pulse energy levels.

TABLE 1.1

| | | Repetition Frequency (Hz) | | | | | | | | | | | | | |
|---|---|---|---|---|---|---|---|---|---|---|---|---|---|---|---|
| | | 5 | 6 | 8 | 10 | 15 | 20 | 25 | 30 | 35 | 40 | 50 | 60 | 70 | 80 |
| Pulse Energy (J) | 0.2 | 1 | 1.2 | 1.6 | 2 | 3 | 4 | 5 | 6 | 7 | 8 | 10 | 12 | 14 | 16 |
| | 0.3 | 1.5 | 1.8 | 2.4 | 3 | 4.5 | 6 | 7.5 | 9 | 10.5 | 12 | 15 | 18 | 21 | 24 |
| | 0.4 | 2 | 2.4 | 3.2 | 4 | 6 | 8 | 10 | 12 | 14 | 16 | 20 | 24 | 28 | 32 |
| | 0.5 | 2.5 | 3 | 4 | 5 | 7.5 | 10 | 12.5 | 15 | 17.5 | 20 | 25 | 30 | 35 | 40 |
| | 0.6 | 3 | 3.6 | 4.8 | 6 | 9 | 12 | 15 | 18 | 21 | 24 | 30 | 36 | 42 | |
| | 0.8 | 4 | 4.8 | 6.4 | 8 | 12 | 16 | 20 | 24 | 28 | 32 | 40 | 48 | 56 | |
| | 1.0 | 5 | 6 | 8 | 10 | 15 | 20 | 25 | 30 | 35 | 40 | 50 | 60 | | |
| | 1.2 | 6 | 7.2 | 9.6 | 12 | 18 | 24 | 30 | 36 | 42 | 48 | 60 | 72 | | |
| | 1.5 | 7.5 | 9 | 12 | 15 | 22.5 | 30 | 37.5 | 45 | 52.5 | 60 | 75 | | | |
| | 1.8 | 9 | 10.8 | 14.4 | 18 | 27 | 36 | 45 | 54 | 63 | 72 | 90 | | | |
| | 2.0 | 10 | 12 | 16 | 20 | 30 | 40 | 50 | 60 | 70 | 80 | 100 | | | |
| | 2.5 | 12.5 | 15 | 20 | 25 | 37.5 | 50 | 62.5 | 75 | 87.5 | 100 | | | | |
| | 3.0 | 15 | 18 | 24 | 30 | 45 | 60 | 75 | 90 | | | | | | |
| | 3.5 | 17.5 | 21 | 28 | 35 | 52.5 | 70 | 87.5 | | | | | | | |

As shown in Table 1.1, the highlighted horizontal axis indicates the overall repetition rates of the output laser pulses generated by one or more laser cavities 141A-D, and the highlighted vertical axis indicates the pulse energy levels of output laser pulses generated by the one or more laser cavities 141A-D. An average power output level of a laser pulse may be obtained by inputting, for example, via the user interface 104, a repetition frequency, and a pulse energy level indicated in a spectrum matrix (e.g., Table 1.1). For example, in order to generate a laser pulse having an average output of 4 Watts (W), a user may input, via the user interface 104, a repetition frequency of 8 Hz and a pulse energy level of 0.5 Joules (J). In one example, in order to generate an output laser pulse having an overall repetition frequency below 10 Hz (e.g., 5 Hz, 6 Hz, 8 Hz, etc.), the controller 110 may automatically generate one or more signals to control a single laser cavity (e.g., any one of the four cavities) to generate the output laser pulse. Additionally or alternatively, the controller 110 may control: two laser cavities to generate an output laser pulse having an overall repetition frequency at 10 Hz to 14 Hz; three or more laser cavities to generate output laser pulses having overall repetition frequencies of 15 Hz to 19 Hz; and four laser cavities to generate output laser pulses having overall repetition frequencies at 20 Hz or higher. Of course, the spectrum matrix may be varied based on the operating capabilities of the medical laser system 100. Further, additional spectrum matrices may be programmed or generated based on different laser applications and/or treatments.

In some embodiments, the user interface 104 may receive control inputs from a user (or an operator). The control inputs may include, for example, pulse energy data (or value), repetition frequency data (or value), and/or pulse mode data (or value) associated with the output laser pulse 160. The pulse energy data and the repetition frequency data may correspond to, for example, one or more parameters listed in one or more discrete spectrum matrices (e.g., PRF matrix shown in Table 1.1) stored in the memory 119. The laser pulse mode data may correspond to one or more laser pulse shapes that may be generated by the medical laser system 100 of this disclosure. For example, one or more laser pulse modes may include a regular pulse, a short pulse, a long pulse, a very long pulse, a dust pulse, and a burst pulse. The PWM module 116 may generate PWM control signals to modulate electric pulse signals in order to generate laser pulses having various modes (or shapes). In one embodiment, one or more parameters associated with the one or more laser pulse modes may be programmed or stored in the memory 119 in order to integrate the parameters of the one or more pulse modes with an existing spectrum matrix (e.g., PRF matrix).

In some embodiments, the one or more pulse modes may be defined as: a short or long pulse with high pulse energy (e.g., approximately 3500 mJ); a short or long pulse with medium pulse energy (e.g., approximately 2000 mJ); and a short or pulse with low pulse energy (e.g., approximate 600 mJ). In some embodiments, a sub-pulse frequency (f) and a pulse profile width (t) of a PWM control signal may be predefined for all modes of laser pulses. Thereafter, the overall electric pulse width ($\tau$) may be adjusted by a user or operator to obtain a desired laser pulse mode. Additionally, laser pulses having different pulse energy levels may be achieved by changing the pulse width ($\tau$) parameter. As discussed above, laser pulses with different pulse energy levels may have the same frequency (f), and approximately the same pulse width (t). That is, the pulse energy may be adjusted based on the change in the sub-pulse duty cycle (p) of a PWM control signal.

Figure 2:
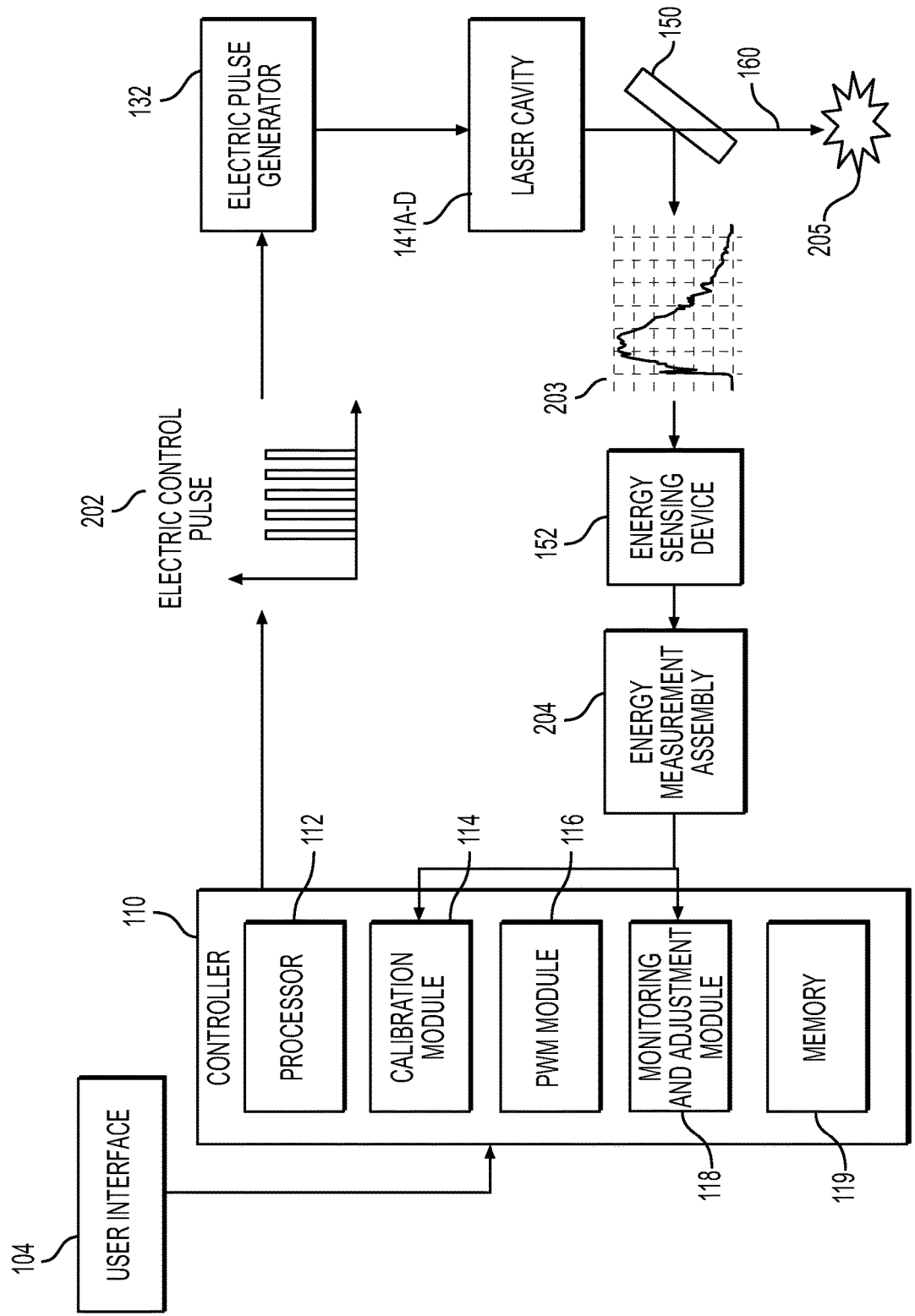
FIG. 2 illustrates an exemplary process of generating laser pulses using the medical laser system of FIG. 1, according to aspects of this disclosure.

FIG. 2 shows an exemplary laser pulse generation process 200 that utilizes techniques to calibrate and dynamically adjust laser pulses having one or more laser pulse modes (or shapes) in accordance with one or more aspects of this disclosure. In order to ensure the accuracy of laser pulses generated by the system 100, the laser pulse energy associated with each working point (or cell) in one or more spectrum matrices (e.g., PRF matrix) must be controlled to be within a certain predetermined tolerance or threshold. In some embodiments, at least two processes may be employed singly or in combination. First, the medical laser system 100 may be calibrated. Second, the medical laser system 100 may provide a function that may dynamically adjust and control (e.g., via a closed-loop control) the laser pulse energy in response to the variations in the working states of one or more of the laser cavities 141A-D.

Still referring to FIG. 2, a user may initiate a calibration process by entering or selecting one or more inputs in the user interface 104. In one exemplary embodiment of process 200, user interface 104 may receive control inputs from a user or an operator. For example, the user may enter a request or input to calibrate a selected laser working point (or laser mode) on one or more discrete spectrum matrices (e.g., pulse energy 0.2 J and repetition frequency of 5 Hz of PRF matrix shown in Table 1.1) stored in memory 119. The calibration module 114 may then generate control signals to initiate a calibration process. The controller 110 may generate an electric control pulse 202 in response to the control signals generated by the calibration module 114. For example, the controller 110 may, for example, by utilizing the PWM module 116, the monitoring and adjustment module 118, and/or the memory 119, generate electric control pulse 202 that may correspond to the selected laser mode (e.g., pulse energy 0.2 J and repetition frequency of 5 Hz of PRF matrix shown in Table 1.1). The electric pulse generator 132 may then generate and transmit electric pumping signals based on the electric control pulse 202 to one or more laser cavities 141A-D. The one or more laser cavities 141A-D may then generate an output laser (or optical) pulse 160 based on the electric pumping signals received from the electric pulse generator 132 to be delivered to a target site 205 (e.g., tissue of a patient) to perform, for example, a medical procedure. In some embodiments, the beam splitter 150 may split the output laser pulse 160 to reflect a portion 203 (e.g., approximately 1%) of the output laser pulse 160 to the energy-sensing device 152.

The energy sensing device 152 may respond to the received portion 203 of the output laser pulse 160 to detect and measure the energy of the portion 203 of the output laser pulse 160. In one embodiment, the energy-sensing device 152 may detect the portion 203 of the output laser pulse 160, for example, in the range of microseconds to milliseconds. The energy sensing device 152 may include a pyroelectric sensor (further described in FIG. 5) that may detect in a relatively large pulse energy range, for example, approximately between 0.1 J and 5 J. The energy sensing device 152 may generate an electrical signal corresponding to the detected energy of portion 203 of the output laser pulse 160 and transmit the electrical signal to the energy measurement assembly 204. The energy measurement assembly 204 may then perform signal transformation and signal amplification to generate a feedback signal based on the received electric signal that may correspond to the detected energy of the portion 203 of the output laser pulse 160. The energy measurement assembly 204 may transmit the feedback signal to calibration module 114 and the monitoring and adjustment module 118 for further processing.

In embodiments, the calibration module 114 may store one or more tables of calibrated pulse parameters based on the laser pulse energy measured by the energy-sensing device 152 and the energy measurement assembly 204 (e.g., EMB) in the memory 119. For example, the following shows an exemplary table of calibrated pulse parameters.

TABLE 1.2

| Pulse Modes | 1 | 2 | 3 |
|---|---|---|---|
| Target Pulse Energy | $E_s(1)$ | $E_s(2)$ | $E_s(3)$ |
| Target EMB Measured Energy | $e_s(1)$ | $e_s(2)$ | $e_s(3)$ |
| Electric Pulse Width | $\tau_s(1)$ | $\tau_s(2)$ | $\tau_s(3)$ |

Each parameter of Table 1.2 may be defined as follows:
E=Target pulse energy;
e=Target EMB Measured pulse energy of a laser pulse; and
τ=Electric pulse width corresponding to the pulse mode. The target EMB measured pulse energy (e), and the electric pulse width (τ) may be determined during the calibration process.

In one embodiment, the calibration process of this disclosure may be performed, for example, in a trial-and-error manner. For example, a user or an operator may operate the system 100 at a selected working point in a spectrum matrix (e.g., the PRF matrix), and adjust the pumping electric energy (e.g., by changing the electric pulse width (τ)) until the output laser pulse energy reaches the target value (e.g., within a predetermined tolerance range). The user may then measure the EMB measured energy value under this condition. The set of parameters (Target pulse energy (E), target EMB measured pulse energy (e), and electric pulse width (τ)) determined based on this exemplary calibration process may be the calibrated results for the selected working point in the spectrum matrix. The same procedure may be performed for all working points in the spectrum matrix to calibrate the medical laser system 100.

Still referring to FIG. 2, the monitoring and adjustment module 118 may receive the feedback signal generated from the energy measurement assembly 204. In some embodiments, the monitoring and adjustment module 118 may perform a closed-loop control based on an algorithm or logic stored in the monitoring and adjustment module 118 and/or in the memory 119. The monitoring and adjustment module 118 may ensure the output laser pulse 160 generated by one or more laser cavities 141A-D are stable and at the required (or calibrated) level. For example, when the monitoring and adjustment module 118 receives measured pulse energy ($e_m$) from the energy measurement assembly 204, the monitoring and adjustment module 118 may perform the following closed-loop control algorithms:

1) Determine the actual energy of the laser pulse based on the measured pulse energy ($e_m$) by comparing $e_m$ with a preset target EMB measured energy $e_s(i)$:
   a) If $e_m$ is between $e_s(n)$ and $e_s(n+1)$, then calculate actual measured energy ($E_m$) in accordance with the following algorithm:

$$E_m = \frac{E_s(n+1) - E_s(n)}{e_s(n+1) - e_s(n)} \cdot [e_m - e_s(n)] + E_s(n)$$

2) Obtain energy error value SE based on the following algorithm:

$$\delta E = E_s(m) - E_m$$

3) Determine an estimated electric pulse width error value based on the following algorithm:

$$\delta\tau = \frac{\tau_s(m+1) - \tau_s(m)}{E_s(m+1) - E_s(m)} \cdot \delta E$$

4) The estimated electric pulse width error value δτ may not be directly added to the preset electric pulse width (e.g., $\tau_s(i)$) to avoid drastic changes in pulse energy. The following damping algorithm may be applied based on a predetermined damping coefficient (g). The new adjusted pulse width delta value Δτ(new) may be determined based on the following algorithm:

$$\Delta\tau(new) = \Delta\tau_s + \delta\tau \cdot g$$

5) The new adjusted electric control pulse width τ(new) may be generated based on the new adjusting pulse width value in accordance with the following algorithm:

$$\tau(new) = \tau_s(i) + \Delta\tau(new)$$

Accordingly, the monitoring and adjustment module 118 may perform, by communicating, for example, with the calibration module 114 and the memory 119, the closed-control loop process (or algorithm) in accordance with the process 200 of this disclosure. For example, the monitoring and adjustment module 118 may dynamically adjust one or more laser pulse parameters (e.g., electric control pulse width τ) to output a more accurate and stabilized output laser pulse 160. That is, the closed-control loop process of this disclosure may dynamically compensate for potential laser energy shifting due to influences that may be caused by potential environmental and/or manufacturing variations.

Figure 3:
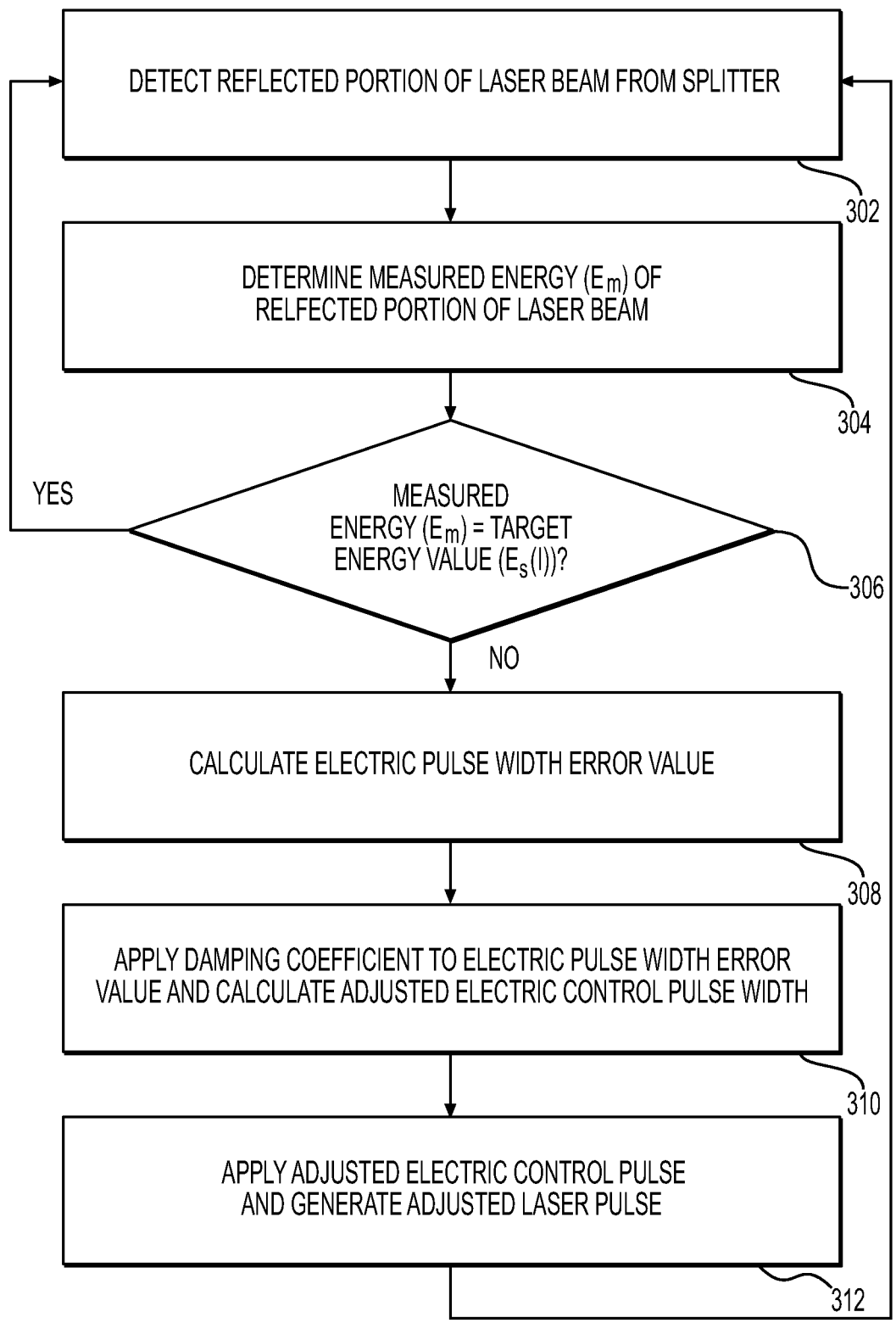
FIG. 3 illustrates a flow chart depicting an exemplary method of generating laser pulse using the laser system of FIG. 1, according to aspects of this disclosure.

FIG. 3 shows an exemplary process 300 for performing laser pulse monitoring and adjustment techniques in accordance with the system and process disclosed in FIGS. 1 and 2. This exemplary process may allow the medical laser system 100 to output laser pulses with consistent and reliable laser energy levels by performing the exemplary closed-control loop process described hereinafter.

At step 302, the energy-sensing device 152 may detect a portion of an output laser beam (or pulse) reflected from the beam splitter 150. In one embodiment, the portion of the output laser pulse may be approximately 1% of the output laser pulse. At step 304, the energy measurement assembly 134 may determine the measured pulse energy ($e_m$) of the reflected portion of the output laser pulse. The energy measurement assembly 134 may transmit the measured pulse energy ($e_m$) to the monitoring and adjustment module 118. At step 306, the monitoring and adjustment module 118 may compare the measured pulse energy ($e_m$) with the target EMB measured energy value ($e_s(i)$) of the output laser pulse. If the measured pulse energy ($e_m$) is approximately the same as the target EMB measured energy value ($e_s(i)$), the process 300 may loop back to step 302 in order to detect a reflected portion of another (or next) laser beam (or pulse) from the beam splitter 150.

Still referring to step 306, if the measured pulse energy ($e_m$) is different from the target EMB measured energy value ($e_s(i)$) (e.g., the difference being greater than a predetermined threshold), the monitoring and adjustment module 118 may calculate the actual measured energy ($E_m$) of the output laser pulse. For example, if the measured pulse energy ($e_m$) is determined to be between one preset target EMB measured energy ($e_s(n)$) and another preset target EMB measured energy ($e_s(n+1)$), the monitoring and adjustment module 118 may calculate the actual measured energy ($E_m$), in accordance with the one or more algorithms of the closed-loop control process described in process 200 of FIG. 2. The monitoring and adjustment module 118 may also calculate the energy error value (δE) based on the actual measured energy ($E_m$). At step 308, the monitoring and adjustment module 118 may calculate an electric pulse width error value (δτ) based on the calculated energy error value (δE). At step 310, the monitoring and adjustment module 118 may apply a damping coefficient (g) to the electric pulse width error value (δτ) to avoid drastic changes in the pulse energy. Further, the monitoring and adjustment module 118 may calculate an adjusted electric control pulse width τ(new). At step 312, the controller 110 may generate and transmit the new, adjusted electric control pulse to the electric pulse generator 132. The electric pulse generator 132 may then generate and transmit one or more electric pumping pulses based on the new adjusted electric control pulse to the one or more laser cavities 141A-D. Process 300 may then loop back to step 302 in order to detect a reflected portion of another (or next) output laser beam (or pulse) from the beam splitter 150.

The calibration techniques and the monitoring and adjustment techniques of the system and processes are disclosed in FIGS. 1-3 may be improved by providing the beam splitter 150 with a relatively constant split ratio. For example, the split ratio of the beam splitter 150 may be relatively constant and not vary with one or more features of the output laser pulses, for example, the pulse energy levels, pulse widths, and/or polarization states of the output laser pulses. In embodiments, the beam splitter 150 may split approximately 1% to 2% of the light from the output laser beam or pulse (e.g., 160) and may reflect the split portion of the output laser pulse in a direction perpendicular to the output laser pulse. However, each laser beam (or pulse) output from different cavities (e.g., one or more laser cavities 141A-D) may have slightly different polarization states and may travel in slightly different directions. As such, the monitoring (or measurement) signals may not be consistent or accurate if the split ratio of the beam splitter 150 varies based on the incident output laser beams with the different polarization states.

In embodiments of this disclosure, an output laser beam may be incident to the beam splitter 150 at an angle of 45° (i.e., the reflected beam will be perpendicular to the main beam). The reflection of a P-polarization component (i.e., parallel to the incident plane) of an output laser beam may be different from that of an S-polarization component (i.e., perpendicular to the incident plane) of the output laser beam. Thus, the overall split ratio of the output laser beam may depend on the polarization state of the output laser beam. In some embodiments of this disclosure, all laser cavities (e.g., laser cavities 141A-D) may share a common target signal value based on the parameters of the output laser pulse (e.g., pulse energy, pulse mode, and pulse repetition rate). As such, in some instances, the monitoring (or measured) signal variations may result between different laser cavities even if the pulse energy of the different laser cavities may be the same due to the different polarization components of the output laser beams.

In embodiments of this disclosure, a polarization-insensitive coating may be applied to the beam splitter 150 in order to improve the consistency of the split ratio of the beam splitter 150. In some embodiments, the beam splitter 150 with a polarization-sensitive coating may yield different reflection (or split) ratios for an S-polarization component of the output laser beam and a P-polarization component of the output laser beam. However, the beam splitter 150 with the polarization-insensitive coatings may yield, for example, in a specified (or selected) small wavelength range, the split ratios for both S and P-polarizations that may be in a relatively close range, for example, approximately ±0.5%. That is, the split ratio difference between the two polarizations may be minimized at the specified wavelength (e.g., 5 Hz) and may also remain small in a range near the specified wavelength. Table 1.3 shows exemplary test results of the split ratio maximum variations in the four cavities (e.g., laser cavities 141A-D), and a comparison between the beam splitter with a polarization-insensitive coating and a polarization-sensitive coating.

TABLE 1.3

| | | Polarization Insensitive Coating | | Polarization Sensitive Coating | |
|---|---|---|---|---|---|
| Pulse Mode | Pulse Energy Level (mJ) | Average Split Ratio (%) | Relative Maximum Ratio Difference (%) | Average Split Ratio (%) | Relative Maximum Ratio Difference (%) |
| Small 5 Hz | 300 | 2.50 | 1.62 | 2.74 | 14.68 |
| Medium 5 Hz | 800 | 2.55 | 6.23 | 2.77 | 8.65 |
| | 1200 | 2.38 | 8.91 | 2.69 | 16.61 |
| | 2400 | 2.37 | 6.45 | 2.8 | 12.76 |
| Large 5 Hz | 4000 | 2.59 | 2.90 | 2.84 | 5.90 |
| Dust 5 Hz | 1000 | 2.56 | 4.65 | 2.77 | 12.11 |
| | 4000 | 2.47 | 6.15 | 2.66 | 7.38 |
| Burst 5 Hz | 1000 | 2.5 | 2.81 | 2.70 | 14.21 |
| | 4000 | 2.53 | 1.82 | 2.78 | 5.97 |

In this example, Table 1.3 shows that the variations due to the influence of different laser beam polarizations may be reduced to less than 10%. Additionally, the split ratio of both S and P-polarizations of the laser beam may have a tolerance based on one or more processes of this disclosure. The tolerance may be independent of the value of the split ratio. That is, the relative split ratio variation may be made smaller by raising the target split ratio. Therefore, a higher split ratio may be specified to improve the output energy variation between the laser cavities 141A-D.

Figure 4A:
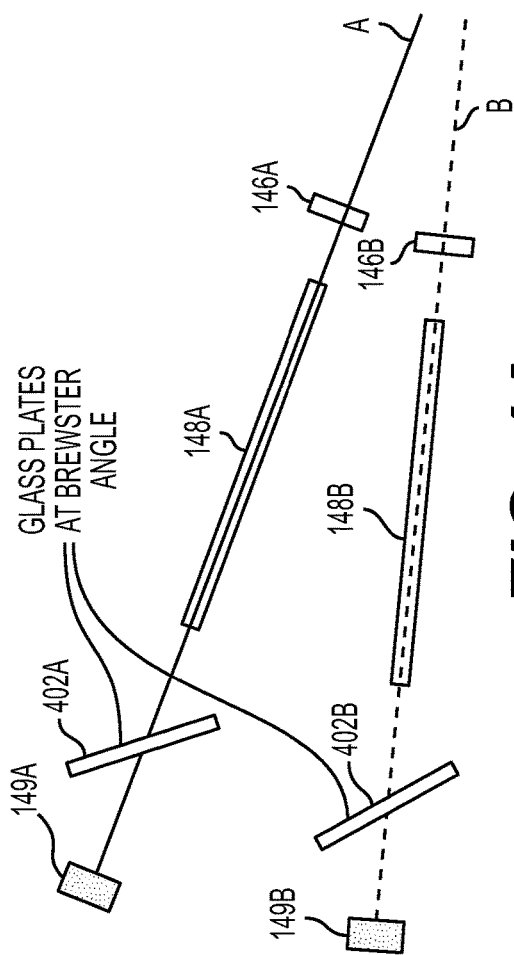
FIG. 4A illustrates exemplary laser cavities of the medical laser system of FIG. 1, according to aspects of this disclosure.

Additionally or alternatively, additional optical components may be utilized to further minimize the variations in the polarization states of the laser beams generated by one or more laser cavities 141A-D. FIG. 4A shows an exemplary laser cavity that may utilize glass plate inserts 402A and 402B to minimize the variations in the polarization states of the laser beams. For example, the glass plate insert 402A may be inserted between the high reflecting window 149A and the laser rod 148A of the laser cavity 141A. Similarly, a glass plate insert 402B may be inserted between the high reflecting window 149B and the laser rod 148B of the laser cavity 141B. Although not shown for brevity, the glass plate inserts may be inserted in a similar manner for each of the laser cavities 141A-D. In one embodiment, the glass plate inserts 402A, and 402B may be inserted inside the laser cavities 141A and 141B so as to form Brewster's angle in relation to the oscillating laser beams in the optical paths A and B. Brewster's angle (also known as the polarization angle) is an angle of incidence at which light with a particular polarization is perfectly transmitted through a transparent dielectric surface, with no reflection. In one embodiment, the glass plate inserts 402A and 402B angled at Brewster's angle may favor the P-polarization laser oscillation in the laser cavities 141A and 141B. That is, the polarization state of the output laser pulse may be controlled consistently for all laser cavities 141A-D. Accordingly, the variations of the split ratio of the beam splitter 150 may be reduced even if the beam splitter 150 may have some residual ratio difference between the two polarization directions.

Figure 4B:
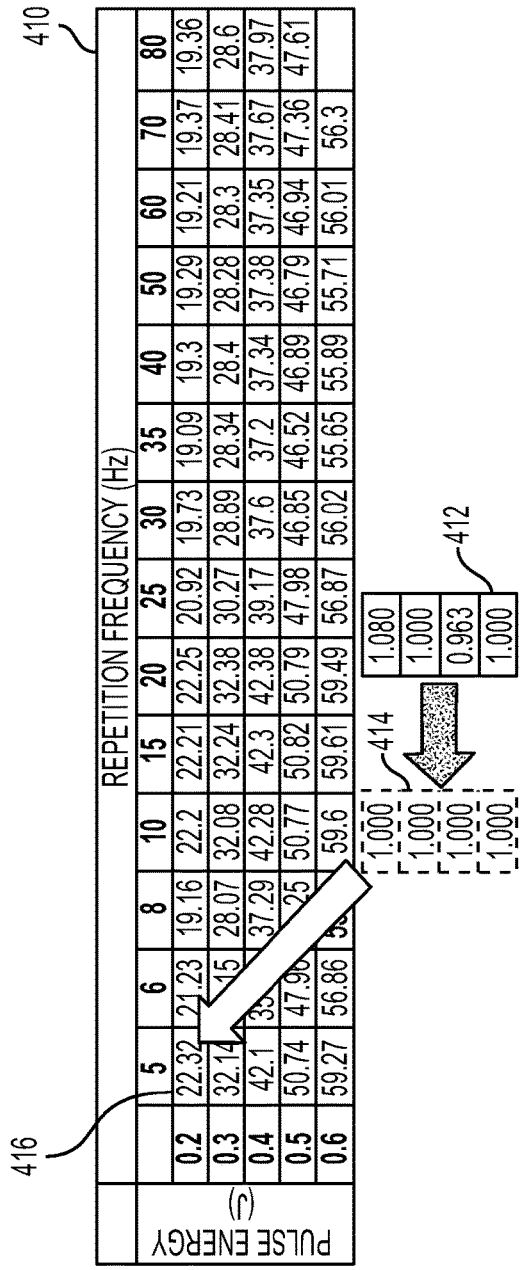
FIG. 4B illustrates an exemplary process of adjusting a laser pulses using the medical laser system of FIG. 1, according to aspects of this disclosure.

Additionally or alternatively, an exemplary parameter compensation method in accordance with this disclosure may be utilized to further minimize the effects of the variations in the polarization states of the laser beams generated by one or more laser cavities 141A-D. FIG. 4B shows a parameter compensation process that may be performed by the controller 110 to compensate for the variations in the split ratios of the beam splitter 150. In one embodiment, four correction parameters may be assigned to each target EMB measurement value ($e_s(n)$) for each laser working point (mode or cell) n in a spectrum matrix 410. The spectrum matrix 410 may include pulse energy and pulse repetition frequencies as the laser parameters. The spectrum matrix 410 may be any spectrum matrix stored or programmed in the memory 119 in accordance with this disclosure and may include a complete spectrum of the available average power output of the system 100. As described in process 200 of FIG. 2, the target EMB measured energy ($e_s(n)$) may be obtained during a calibration process.

Still referring to FIG. 4B, each of the four correction factor parameters (e.g., $\rho 1(n)$, $\rho 2(n)$, $\rho 3(n)$, $\rho 4(n)$) may correspond to each of the four different laser cavities 141A-D. The four correction factor parameters may be correction ratios that correspond to the measured energy ($e_m$) values for the laser cavities 141A-D, with default values being 1 for all correction factors. For example, if the measured energy ($e_m$) of a working laser point during a closed-loop control process (e.g., process 300) has errors ($\delta E$) in the actual output laser pulses based on the target EMB measured energy ($e_s(n)$), the four correction parameters may be utilized to adjust the measured energy ($e_m$) values. In the example process shown in FIG. 4B, the target EMB measured energy ($e_s(n)$) value for an output laser mode 416, for example, of 5 Hz and 200 mJ maybe 22.32 W. In one embodiment, a four-element correction factor table 414 may be associated with this laser mode, with default values for the four laser cavities 141A-D being 1. If the closed-loop process (e.g., process 300) results in errors ($\delta E$) in the actual output laser pulse, for example, approximately 8% above the target in the laser cavity 141A and approximately 4% below the target in cavity 141C, then the correction parameters for the laser cavities 141A and 141C may be changed to approximately 1.08 and 0.963, as shown in a four-element correction table 412. The following algorithm may be utilized to calculate the actual measured pulse energy ($E_m$) in accordance with the correction factor parameters ($\rho i(n)$) and the measured energy ($e_{(i)m}$) in the closed-loop processes as disclosed in FIGS. 2 and 3:

$$E_{(i)m} = \frac{E_s(n+1) - E_s(n)}{e_s(n+1) - e_s(n)} \cdot [e_{(i)m} \cdot \rho i(n) - e_s(n)] + E_s(n)$$

The errors due to the variations between the laser cavities 141A-D may be corrected effectively by utilizing the correction parameters and the algorithm described above.

In some embodiments, the polarization-insensitive coating, the glass inserts (e.g., 402A and 402B) at Brewster's angle, and the parameter compensation method discussed above may be utilized singly or in combination to improve the accuracy of the output laser pulse measurement. For example, the accuracy requirement for the laser pulse energy may be set to be approximately within ±10% of the split ration variation. In this example, a polarization-insensitive coating may be utilized to improve the consistency of the split ratio of the beam splitter. In another example, where a higher accuracy may be required, in addition to the polarization-insensitive coating, the parameter compensation method in accordance with FIG. 4B may be utilized. In this example, the selected split ratio of the beam splitter 150 may be smaller than, for example, 1%. This example may reduce additional hardware costs. In yet another example, the polarization-insensitive coating, the glass plate inserts (e.g., 402A and 402B) arranged at Brewster's angle in relation to the laser beams, and the parameter compensation method in accordance with FIG. 4B may be utilized together in combination. In this example, consistent polarization states of the laser output from all laser cavities 141A-D may be produced.

Figure 5:
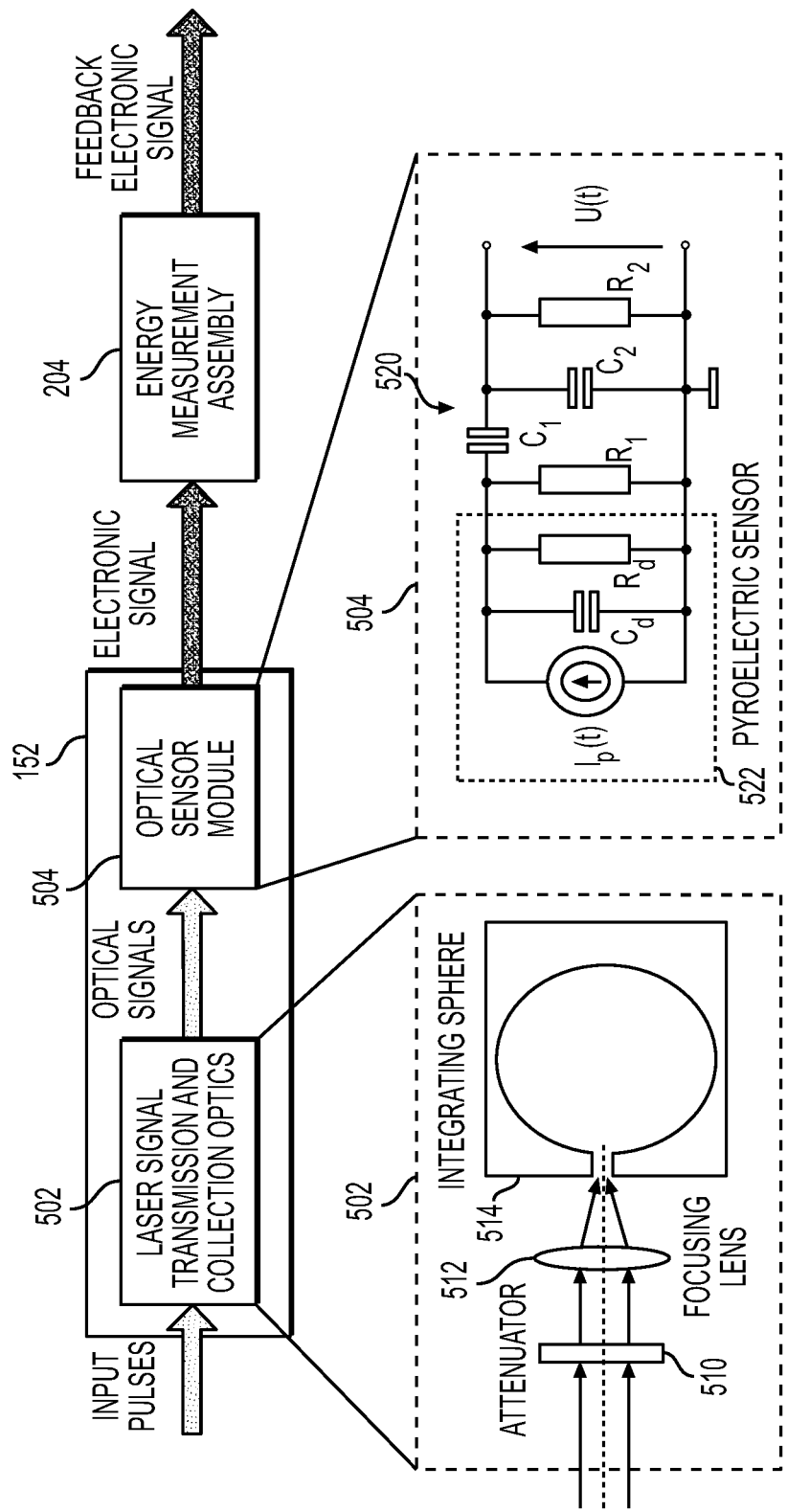
FIG. 5 illustrates an exemplary process of measuring the energy of a laser pulse using the medical laser system of FIG. 1, according to aspects of this disclosure.

FIG. 5 shows a laser pulse energy measurement process 500 utilizing the laser energy sensing device 152 and the energy measurement assembly 204 in accordance with this disclosure. In some embodiments, the laser energy sensing device 152 may receive portions of output laser pulses reflected by the beam splitter 150. The laser energy sensing device 152 may include laser signal transmission and collection optics 502 and an optical sensor module 504. In embodiments, the laser signal transmission and collection optics 502 may include an optical attenuator 510, a focusing lens 512, and an integrating sphere 514.

The laser signal transmission and collection optics 502 may transform a reflected portion (e.g., an input pulse) of an output laser pulse into a signal form that may be detected by the optical sensor module 504. In some examples, the output laser pulses that reach the optical sensor module 504 may be stronger than what can be tolerated by the sensors (e.g., pyroelectric sensor 522) in the optical sensor module 504. Thus, the optical attenuator 510 may be utilized to add loss to the input pulse to achieve intensity matching of signals within an appropriate sensing range. For example, a neutral optical filter may be utilized as the optical attenuator 510. The optical attenuator 510 may transmit a laser pulse in the range of 10% to 30%, depending on the split ratio of the beam splitter 150. The focusing lens 512 and the integrating sphere 514 may form a sub-assembly that may convert the incident laser pulse into diffused light in the integrating sphere 514. The diffused light may then be absorbed by the sensors (e.g., pyroelectric sensor 522) of the optical sensor module 504 that may be arranged on a sidewall of the integrating sphere 514.

In some embodiments, the light energy received by a sensor (e.g., pyroelectric sensor 522) located on a wall of the integrating sphere 514 may be proportional to the input laser pulse energy entering the integrating sphere 514. That is, the ratio of the input laser pulse energy and the detected light energy may be relatively fixed. Any distortion and delay of the light energy signal received by the sensor of the optical sensor module 504 may be negligible if the time delay or change in the light energy signal is on the order of, for example, nanoseconds. For example, the time constant of the delay may vary with the diameter of the integrating sphere 514. The diameter of the integrating sphere 514 of this disclosure may be, for example, approximately 30 mm. Accordingly, the time constant associated with the integrating sphere 514 may be less than, for example, 50 nanoseconds. In one embodiment, the integrating sphere 514 may be configured to be integrated with multiple sensors to enhance the reliability of the energy-sensing device 152. In some embodiments, the requirement on the direction accuracy of the input laser pulse may be reduced. For example, the input aperture of the integrating sphere 514 may be, for example, 6 mm, allowing the incident angle tolerance to be relatively large. Consequently, the positioning of the beam splitter 150 in the system 100 may be flexible and convenient.

Still referring to FIG. 5, the optical sensor module 504 may be assembled on a circuit board. The optical sensor module 504 may comprise an equivalent circuit 520. The equivalent circuit 520 may comprise an optical sensor 522, capacitors (e.g., $C_d$, $C_1$, $C_2$), and resistors (e.g., $R_d$, $R_1$, $R_2$) arranged as shown in FIG. 5. In one embodiment, the optical sensor 522 may be a pyroelectric sensor. The pyroelectric sensor (i.e., the optical sensor 522) may detect pulsed optical signals with a pulse duration in the range of, for example, microseconds to milliseconds. In one embodiment, the pyroelectric sensor may be a capacitor formed by depositing metal electrodes on both surfaces of a thin slice of pyroelectric material. The absorption of the radiation pulse of power P(t) by the pyroelectric material may result in a change in its temperature with the value of ΔT, which may yield a displacement current $I_p(t)$. The current $I_p(t)$ may be determined based on the following algorithm:

$$I_p = p \cdot \frac{dT}{dt} \cdot S$$

In accordance with the above algorithm: the pyroelectric coefficient may be defined as (p); the speed of temperature changes of the pyroelectric material may be defined as (dT/dt); and the surface area of the sensor electrode may be defined as (S). In some examples, the current generated by the optical sensor 522 may vary with the temperature change of the sensor material (e.g., pyroelectric material). Thus, the optical sensor 522 circuit may be designed with an electric time constant that may be smaller than the thermal time constant of the optical sensor 522 and may have an electric time constant that is larger than the pulse width of the laser pulse signals. Accordingly, the rate of temperature changes in the pyroelectric material may be linearly dependent on the power of radiation P(t) falling on the pyroelectric material of the optical sensor 522, as described in the following algorithm:

$$\frac{dT}{dt} \propto P$$

Therefore, the current generated by the optical sensor 522 may also be proportional to the signal power falling on the optical sensor 522, as shown in the following algorithm:

$$I_p(t) = \alpha \cdot P$$

In one embodiment, the voltage signal U'(t) (before output coupling capacitor C1) may be determined by integrating the current Ip of the current source. As such, the relationship between the voltage signal U'(t) and the detected energy of the signal may be derived in accordance with the following algorithm:

$$U'(t) = \alpha \int_0^t P(\tau) d\tau$$

Accordingly, the voltage after the coupling capacitor C1, denoted as U(t), may be expressed by the following algorithm:

$$U(t) = \frac{dU'(t)}{dt} = \alpha \cdot P(\tau)$$

In one embodiment, in order to enhance the signal detecting reliability, multiple pyroelectric sensors yielding multiple channels may be used as the optical sensor 522. For example, each channel of the pyroelectric sensors may be arranged parallel to each other and maybe located in two symmetrical places of the integrating sphere 514. In embodiments, the signals sent by the two pyroelectric sensors may have the same allowed tolerance. Further, the two pyroelectric sensors may serve as verification and confirmation for the measurement and monitoring functions of this disclosure. Furthermore, the output generated by the equivalent circuit 520 may be approximately proportional to the power of the output laser pulse and may be input to the energy measurement assembly 204.

Figure 6:
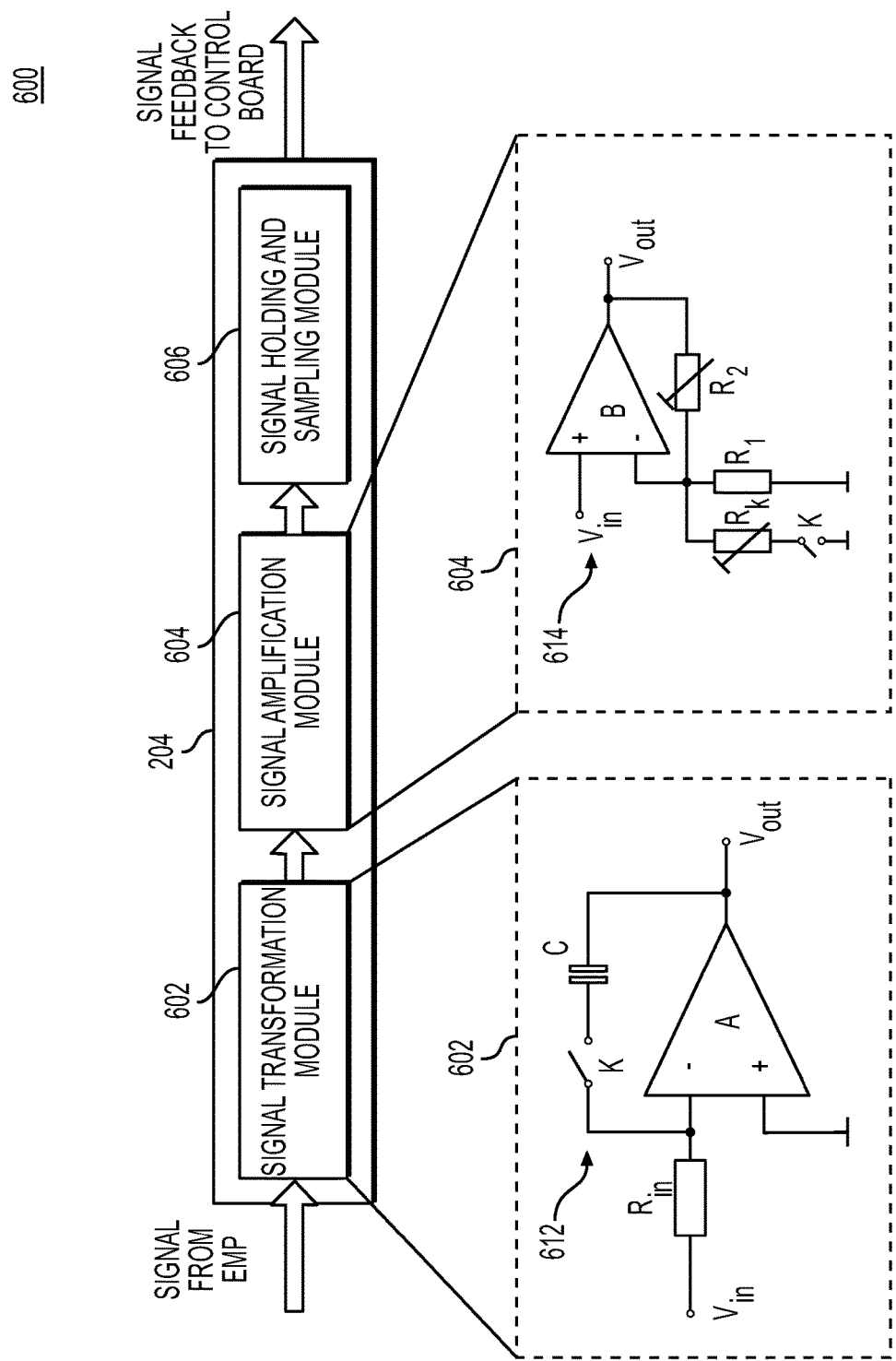
FIG. 6 illustrates another exemplary process of measuring the energy of a laser pulse using the medical laser system of FIG. 1, according to aspects of this disclosure.

FIG. 6 shows an exemplary process 600 utilizing one or more electronic circuits of the energy measurement assembly 204 to convert the signals received from the equivalent circuit 520 into signals that may be translated into indicators of pulse energy levels of the output laser pulses generated by the system 100 of this disclosure. The energy measurement assembly 204 may include a signal transformation module 602, a signal amplification module 604, and a signal holding and sampling module 606.

In embodiments, the signal transformation module 602 may convert the signals received from the equivalent circuit 520 into a feedback signal form that may correspond with the output laser pulses generated by the system 100. The signal transformation module 602 may comprise an inverting operational amplifier circuit 612 configured with two processing options, for example, amplification of input signals (e.g., Vin) or integration of the input signals ($V_{in}$). The inverting amplifier circuit 612 may include a resistor ($R_{in}$), a switch (K), a capacitor (C), and an amplifier A. In one embodiment, when the capacitor C is not electrically connected to the amplifier circuit 612, the inverting amplifier circuit 612 may function as an inverting amplifier. Alternatively, when the capacitor C is electrically connected to the inverting amplifier circuit 612, the inverting amplifier circuit 612 may function as an integrator circuit. The switch K may be configured to switch on and off in accordance with one or more control signals received from the controller 110 of the system 100 based on one or more setting parameters. In one embodiment, when the amplification function is selected by the signal transformation module 602, the output signal ($V_{out}$) (e.g., the feedback signal) may be proportional to the power of the input signal with an amplified amplitude. However, if the integration functionality is selected by the signal transformation module 602, the output signal ($V_{out}$) may be proportional to the energy of the input signal, while the amplitude remains smaller than that amplitude generated during the amplification function.

Still referring to FIG. 6, the signal amplification module 604 may receive transformed signals (e.g., the feedback signal) from the signal transformation module 602. The signal amplification module 604 may include a non-inverting amplifier circuit 614. The non-inverting amplifier circuit 614 may include a resistor (R1), variable resistors (RK and Rx), a switch K, and an amplifier B. The non-inverting amplifier circuit 614 may include two gain adjustment components that may be adjusted separately. That is, the gain of the non-inverting amplifier circuit 614 may be changed by: 1) adjusting the resistance of $R_2$ in the closed-loop; and 2) switching on resistor $R_K$ and tuning its resistance. The effects of adjusting the resistance of the resistor $R_2$ may have a universal effect on the non-inverting amplifier circuit 614. That is, the gain changes yielded by adjusting the resistance of the resistor $R_2$ may be applied to all input signals ($V_{in}$). In contrast, the effects of the change in the $R_K$ may be controlled to be switched on or off by the switch K. In one embodiment, the overall gain of the non-inverting amplifier circuit 614 may be the combined results of adjusting the resistors $R_2$ and $R_K$. The resistor $R_2$ may be utilized to adjust the universal gain in general, affecting all input signals that need to be amplified. The resistor RK may be adjusted optionally, affecting input signals when the switch K is on. As such, two different gains, for example, lower gain or higher gain, may be provided based on the level of input signal intensities.

Still referring to FIG. 6, the signal holding and sampling module 606 may hold the maximum value of the processed signal (e.g., an amplified feedback signal) received from the signal amplification module 604 until a signal sampling occurs. Thereafter, the sampled signal value may be sent to the controller 110 of the system 100 for further calculation and processing. The sampled signal value may represent either peak power or the pulse energy of the input laser signals, depending on the selected function of the signal transformation module 602. The magnitude of the sampled value may depend on the overall gain set in the signal amplification module 604. After the signal sampling of one laser pulse, the controller 110 of the system 100 may transmit a command signal to reset all the circuits in the signal transformation module 602 and the signal amplification module 604 so as not to affect the next laser pulse based on the previous setting.

In some embodiments, the functionality of the signal transformation module 602 and the signal amplification module 604 may be utilized singly or in combination. The monitoring and adjustment module 118 may perform the feedback signal generation over a wide pulse energy range, for example, from 100 mJ to over 4 J. In one embodiment, the signals received from the optical sensor module may be processed only by the amplification functions of the signal transformation module 602 and the signal amplification module 604. In this mode, the peak value of the processed signal that may be provided by the signal holding and sampling module 606 may be a value that is close to the peak power of the signal received from the optical sensor module 504. As such, the lower gain mode of the signal amplification module 604 may be utilized for laser pulses with low laser pulse energy levels. In another embodiment, the signal received from the optical sensor module 504 may be integrated by the signal transformation module 602 and then amplified by signal amplification module 604 with a lower gain. This mode may be utilized for signal pulses with large laser pulse energy levels since the integration function of the signal transformation module 602 may attenuate the intensity of the laser pulse to a certain level, and then the attenuated signal may be amplified by the signal amplification module 604 to the desired range. In yet another embodiment, the integrated signal from the signal transformation module 602 may be amplified in the signal amplification module with a higher gain. This mode may be utilized for signals with medium laser pulse energy levels as well as to low laser energy pulse energy levels. In embodiments, all laser modes (or working points) in the spectrum matrices of this disclosure may be re-grouped into sub-sets based on the energy ranges of the laser outputs, for example, low, medium, and high energy levels. Further, different energy measurement assembly 204 modes, as described above, may be adopted based on different laser pulse energy ranges. As such, the monitored laser signal values may be expanded over various ranges for all sub-sets to improve the resolution of the closed-loop control process of this disclosure.

In one example, in the signal transformation module 602, signals for the laser pulses with low energy levels may be amplified without going through the integration function, and the laser pulses with higher energy levels may be integrated first. However, in both modes, the same gained by the same amount in the signal amplification module 604. In this example, the signal value ranges of the laser pulses with lower energy may be expanded and, at the same time, may ensure that the signal values for the rest of the pulses are in the allowed ranges. For example, the whole range of allowed values may be from 1% to 100%. In this example, the signal values for low energy pulse may be in the range of 20% to 60%, and the values for other pulses may be between 15% and 80%. As such, the signal values may have enough margins from the boundaries on both sides.

In another example, all signals may be integrated in the signal transformation module 6-2 but amplified in the signal amplification module 604 with different gains. A higher gain may be applied for the amplification of signals for low-energy pulse sub-sets. In this example, all signals may have the same physical meaning (i.e., same pulse energy). The signal values may also be expanded to approximately the same range, providing sufficient resolutions for the closed-loop control process.

In addition to the two examples discussed above, additional implementations may be derived. For example, one or more functions of the signal transformation module 602 may be utilized for the input signals. That is, integration only for higher energy pulses (medium and high), and the universal gain in the signal amplification module 604, which may allow the maximum signal values beyond the upper limit of the allowed signal value range. Further, an additional gain may be added to provide the low and medium energy pulses with a higher overall gain of amplification.

Figure 7:
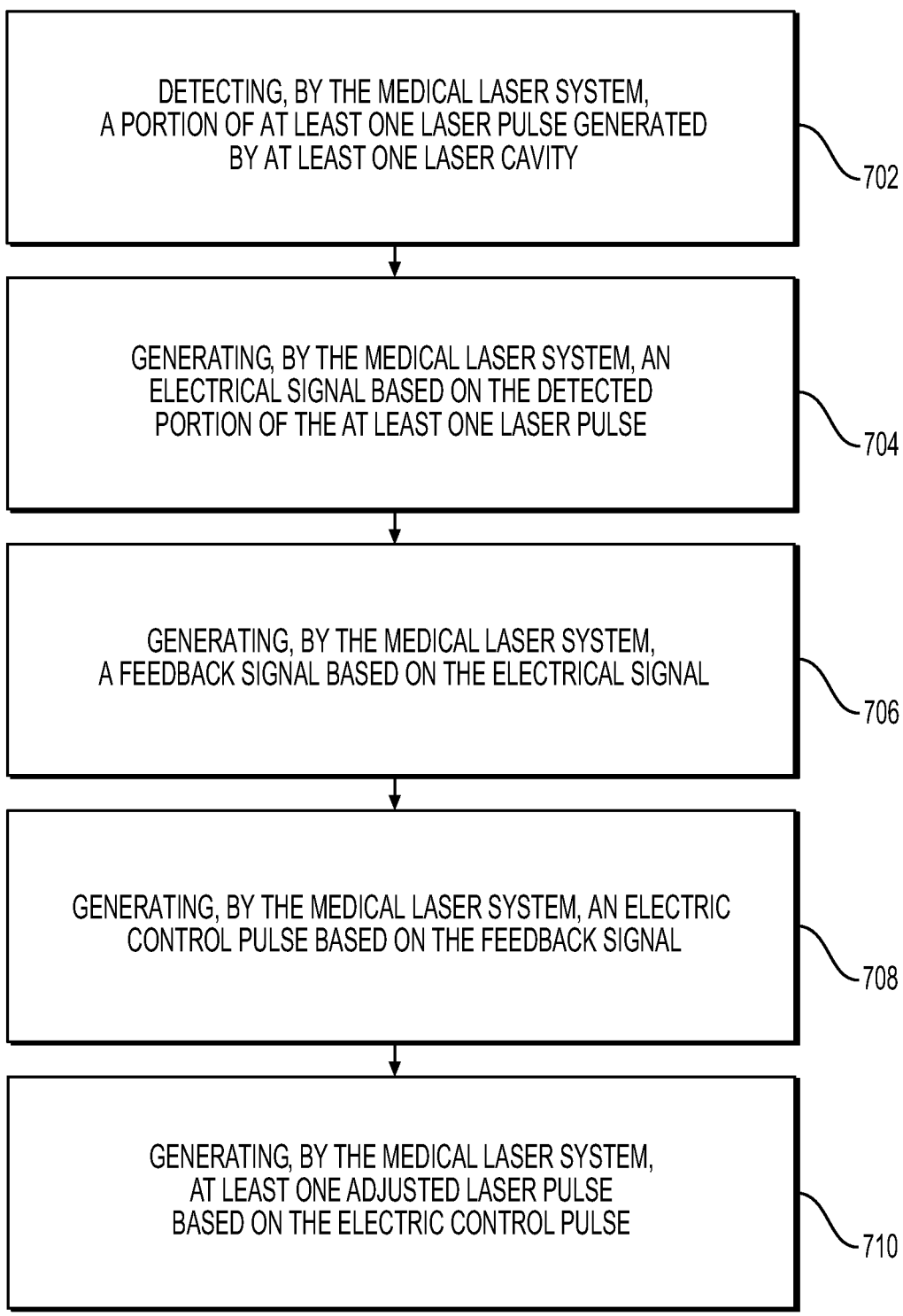
FIG. 7 illustrates a flow chart depicting another exemplary method of generating laser pulses using the medical laser system of FIG. 1, according to aspects of this disclosure.

FIG. 7 shows an exemplary process 700 calibrating, monitoring, and adjusting laser pulses generated by the system 100 by utilizing the calibration and monitoring and adjustment techniques in accordance with the system and processes disclosed in FIGS. 1-6. This exemplary process may allow the system 100 to output calibrated and/or dynamically adjusted laser pulses for medical applications or treatments on target features, such as tissues of a subject (e.g., patient).

At step 702, the medical laser system 100 may detect a portion of at least one laser pulse generated by at least one laser cavity (e.g., laser cavity 141A-D). The portion of at least one laser pulse may be detected by an energy-sensing device 152. At step 704, the medical laser system 100 may generate an electrical signal based on the detected portion of at least one laser pulse. At step 706, the medical laser system 100 may generate a feedback signal based on the electrical signal. In one embodiment, the feedback signal may be generated by transforming and amplifying the electrical signal via the signal transformation module 602 and the signal amplification module 604, respectively. Further, the feedback signal may be generated by switching a mode of an inverting operational amplifier circuit of a signal transformation module between an amplification mode and an integration mode. Furthermore, the feedback signal may be generated by adjusting a gain of a non-inverting amplifier circuit of a signal amplification module by adjusting the resistance of one or more resistors in the non-inverting amplifier circuit. In one embodiment, the medical laser system 100 may calibrate one or more laser modes based on the feedback signal and at least one spectrum matrix.

At step 708, the medical laser system 100 may generate an electric control pulse based on the feedback signal. In one embodiment, the electric control pulse may be generated by the monitoring and adjustment module 118. The electric control pulse may be generated based on a comparison between the feedback signal and a target laser energy level. Further, the electric control pulse may be generated based on an electric pulse width error value based on the comparison between the feedback signal and the target laser energy level. Furthermore, the electric control pulse signal may be generated by determining an adjusted electric control pulse width based on the pulse width error value. At step 710, the medical laser system 100 may generate at least one adjusted laser pulse based on the electric control pulse. In one embodiment, the medical laser system 100 may generate at least one adjusted laser pulse via multiple laser cavities (e.g., laser cavities 141A-D). In one embodiment, the medical laser system 100 may perform a closed-loop control based on the electrical signal based on the detected portion of the at least one laser pulse and the feedback signal. In one embodiment of the closed-loop control, the medical laser system 100 may switch a mode of an inverting operational amplifier circuit (e.g., 612) of a signal transformation module (e.g., 602) between an amplification mode and an integration mode. In another embodiment, the medical laser system 100 may adjust a gain of a non-inverting amplifier circuit (e.g., 614) of a signal amplification module (e.g., 604) by adjusting the resistance of one or more resistors in the non-inverting amplifier circuit.

The medical laser system 100 of this disclosure performs calibration and dynamic monitoring and adjustment techniques for generating consistent and accurate laser pulses. For example, by calibrating and performing a closed-control loop process in accordance with this disclosure, potential laser energy shifting due to influences that may be caused by potential environmental and/or manufacturing variations may be compensated. As such, output laser pulses with consistent and reliable laser energy levels may be produced for each output laser pulse.

It will be understood that reference is made to a number of cavities and/or mirrors in the medical laser system 100. It will be understood that the devices are not limited to this number and may change according to the requirement of the medical laser system 100. Further, while reference is made to a medical/surgical laser system, the laser pulse technique described herein is not limited to a medical/surgical laser system and may be used with any laser system.

It will be apparent to those skilled in the art that various modifications and variations may be made in the disclosed systems and methods without departing from the scope of the disclosure. It should be appreciated that the disclosed system may include various suitable computer systems and/or computing units incorporating a plurality of hardware components, such as, for example, a processor and non-transitory computer-readable medium, that allow the devices to perform one or more operations during a procedure in accordance with those described herein. Other aspects of the disclosure will be apparent to those skilled in the art from consideration of the specification and practice of the features disclosed herein. It is intended that the specification and examples be considered exemplary only.

It should be appreciated that the controller 110 in FIG. 1 may be any computing device. The user interface 104 also may include input and output ports to connect with input and output devices such as keyboards, mice, touchscreens, monitors, displays, etc. Of course, the various system functions may be implemented in a distributed fashion on a number of similar platforms to distribute the processing load. Alternatively, the systems may be implemented by appropriate programming of one computer hardware platform.

In one embodiment, any of the disclosed systems, methods, and/or graphical user interfaces may be executed by or implemented by a computing system consistent with or similar to the descriptions herein. Although not required, aspects of this disclosure are described in the context of computer-executable instructions, such as routines executed by a data processing device, e.g., a server computer, wireless device, and/or personal computer. Those skilled in the relevant art will appreciate that aspects of this disclosure can be practiced with other communications, data processing, or computer system configurations, including Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "computing device," and the like, are generally used interchangeably herein, and refer to any of the above devices and systems, as well as any data processor.

Aspects of this disclosure may be embodied in a special purpose computer and/or data processor that is specifically programmed, configured, and/or constructed to perform one or more of the computer-executable instructions explained in detail herein. While aspects of this disclosure, such as certain functions, are described as being performed exclusively on a single device, this disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

Aspects of this disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer-implemented instructions, data structures, screen displays, and other data under aspects of this disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit-switched, or other scheme).

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While principles of this disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered limited by the foregoing description.

It will be apparent to those skilled in the art that various modifications and variations can be made to the disclosed system without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical laser system for outputting laser pulses, the system comprising:
   at least one laser cavity configured to generate at least one laser pulse;
   a rotating mirror configured to receive and reflect the at least one laser pulse;
   a beam splitter configured to receive and reflect a portion of the at least one laser pulse received from the rotating mirror;
   an energy-sensing device configured to detect the portion of the at least one laser pulse;
   an energy measurement assembly configured to generate a feedback signal based on the portion of the at least one laser pulse detected by the energy-sensing device;
   a controller configured to generate an electronic control pulse based on the feedback signal received from the energy measurement assembly to generate at least one adjusted laser pulse; and
   a memory storing at least one spectrum matrix that correlates a plurality of frequencies specified on a first axis and a plurality of pulse energies on a second axis to an average power output of the medical laser system,
   wherein the medical laser system is configured to calibrate one or more laser modes based on the feedback signal and the at least one spectrum matrix.

2. The system of claim 1, wherein the controller comprises:
   a monitoring and adjustment module configured to perform a closed-loop control based on the feedback signal.

3. The system of claim 1, wherein the controller is configured to generate the electronic control pulse based on a comparison between the feedback signal and a target laser energy level.

4. The system of claim 3, wherein the controller is configured to generate the electronic control pulse based on a pulse width error value calculated based on the feedback signal and the target laser energy level.

5. The system of claim 1, wherein the adjusted laser pulse is generated by adjusting a pulse width level of a laser pulse based on the feedback signal.

6. The system of claim 1, wherein the at least one adjusted laser pulse is generated based at least on one or more correction parameters associated with the at least one laser cavity.

7. The system of claim 1, wherein the energy-sensing device comprises laser collection optics, the laser collection optics including at least one of an attenuator, a focusing lens, or an integrating sphere.

8. The system of claim 1, wherein the energy-sensing device comprises an optical sensor module configured to be attached to laser collection optics, the optical sensor module including a pyroelectric sensor, and a sensor circuit board.

9. The system of claim 1, wherein the energy-sensing device is configured to generate an electrical signal based on the detected portion of at least one laser pulse.

10. The system of claim 1, wherein the energy measurement assembly comprises a signal transformation module configured to receive an electrical signal from the energy-sensing device, the signal transformation module including an inverting operational amplifier circuit;
    a signal amplification module coupled to the signal transformation module, the signal amplification module including a non-inverting amplifier circuit; and
    a signal holding and sampling module coupled to the signal amplification module.

11. The system of claim 10, wherein the signal transformation module is configured to switch a mode of the inverting operational amplifier circuit between an amplification mode and an integration mode.

12. The system of claim 10, wherein the signal amplification module is configured to adjust a gain of the non-inverting amplifier circuit by adjusting the resistance of one or more resistors in the non-inverting amplifier circuit.

13. The system of claim 1, wherein the at least one laser cavity comprises four laser cavities.

14. The system of claim 1, wherein each of the at least one laser cavity comprises a glass plate arranged at a Brewster Angle.

15. The system of claim 1, wherein the beam splitter comprises a polarization-insensitive coating.

16. A method of controlling laser pulses of a medical laser system, the method comprising:
    detecting, by the medical laser system, a portion of at least one laser pulse generated by at least one laser cavity;

generating, by the medical laser system, an electrical signal based on the detected portion of the at least one laser pulse;

generating, by the medical laser system, a feedback signal based on the electrical signal;

accessing, by the medical laser system, at least one spectrum matrix that correlates a plurality of frequencies specified on a first axis and a plurality of pulse energies on a second axis to an average power output of the medical laser system;

generating, by the medical laser system, an electric control pulse based on the feedback signal and the at least one spectrum matrix; and generating, by the medical laser system, at least one adjusted laser pulse based on the electric control pulse.

17. The method of claim 16, further comprising:

calibrating, by the medical laser system, one or more laser modes based on the feedback signal and the at least one spectrum matrix; and performing, by the medical laser system, a closed-loop control based on the electrical signal based on the detected portion of the at least one laser pulse and the feedback signal;

generating, by the medical laser system, the electric control pulse based on a comparison between the feedback signal and a target laser energy level; and generating, by the medical laser system, the electric control pulse based on a pulse width error value based on the comparison between the feedback signal and the target laser energy level; and generating, by the medical laser system, the electric control pulse by determining an adjusted electric control pulse width based on the pulse width error value.

18. The method of claim 16, further comprising:

generating, by the medical laser system, the at least one adjusted laser pulse based at least on one or more correction parameters associated with the at least one laser cavity.

19. The method of claim 16, further comprising:

generating, by the medical laser system, the at least one adjusted laser pulse via multiple laser cavities; and generating, by the medical laser system, the feedback signal by:

switching, by the medical laser system, a mode of an inverting operation amplifier circuit of a signal transformation module between an amplification mode and an integration mode; and adjusting, by the medical laser system, a gain of a non-inverting amplifier circuit of a signal amplification module by adjusting a resistance of one or more resistors in the non-inverting amplifier circuit.

20. A non-transitory computer-readable medium storing instructions for controlling laser pulses of a medical laser system, the instructions, when executed by one or more processors, causing the one or more processors to perform operations comprising:

transmitting a control signal to detect a portion of at least one laser pulse generated by at least one laser cavity;

receiving an electrical signal based on the detected portion of the at least one laser pulse;

generating a feedback signal based on the electrical signal;

generating an electric control pulse based on the feedback signal;

generating at least one adjusted laser pulse based on the electric control pulse;

calibrating one or more laser modes based on the feedback signal and at least one spectrum matrix, wherein the spectrum matrix correlates a plurality of frequencies specified on a first axis and a plurality of pulse energies on a second axis to an average power output of the medical laser system; and performing a closed-loop control based on the electrical signal based on the detected portion of the at least one laser pulse and the feedback signal.

* * * * *